(12) United States Patent
Soukka et al.

(10) Patent No.: US 7,569,355 B2
(45) Date of Patent: Aug. 4, 2009

(54) HOMOGENEOUS LUMINESCENCE ENERGY TRANSFER BIOASSAY

(76) Inventors: Tero Soukka, Sarikatu 3E121, FI-20540 Turku (FI); Harri Härmä, Sirkkalankatu gbA1, FI-20500 Turku (FI); Timo Lövgren, Hakamäentie 57, FI-21610 Kirjala (FI)

( * ) Notice: Subject to any disclaimer, the term of this patent is extended or adjusted under 35 U.S.C. 154(b) by 544 days.

(21) Appl. No.: 11/148,315

(22) Filed: Jun. 9, 2005

(65) Prior Publication Data

US 2005/0272084 A1 Dec. 8, 2005

Related U.S. Application Data

(63) Continuation-in-part of application No. PCT/FI2004/000091, filed on Feb. 24, 2004.

(30) Foreign Application Priority Data

Mar. 28, 2003 (FI) .................................. 20030460

(51) Int. Cl.
*G01N 33/53* (2006.01)
*G01N 33/543* (2006.01)

(52) U.S. Cl. .......................... 435/7.21; 435/6; 435/7.1; 435/7.92; 436/501; 436/518

(58) Field of Classification Search ...................... None
See application file for complete search history.

(56) References Cited

U.S. PATENT DOCUMENTS

| | | | | |
|---|---|---|---|---|
| 5,891,656 A | * | 4/1999 | Zarling et al. ............... | 435/7.92 |
| 5,998,146 A | * | 12/1999 | Latva et al. ................... | 435/6 |
| 6,159,686 A | | 12/2000 | Kardos et al. .................. | 435/6 |
| 6,444,476 B1 | | 9/2002 | Morgan ....................... | 436/172 |
| 2002/0119498 A1 | | 8/2002 | Joung et al. .................. | 435/7.2 |

FOREIGN PATENT DOCUMENTS

| | | | |
|---|---|---|---|
| WO | WO 89/11868 | * | 12/1989 |
| WO | WO 96/01297 | | 1/1996 |
| WO | WO 98/15830 | | 4/1998 |
| WO | WO 02/44725 | | 6/2002 |
| WO | WO 02/44725 A1 | * | 6/2002 |
| WO | WO 03/074630 | | 9/2003 |

OTHER PUBLICATIONS

Niedbala et al. (Analytical Biochemistry, vol. 293, 2001, pp. 22-30).*
Lee et al. (Cytometry, vol. 21, 1995, pp. 120-128).*
Soukka et al., "Novel Homogeneous Assay Technology Based on Up-Converting Nanophosphors," (Univ. Of Turku Apr. 13, 2005).
Soukka et al., "Novel Homogeneous Assay Technology Based On Up-converting Nanophosphors," (Univ. Of Turku Apr. 13, 2005).

* cited by examiner

*Primary Examiner*—Lisa V Cook
(74) *Attorney, Agent, or Firm*—James C. Lydon (57) ABSTRACT

A homogeneous bioassay including a first group labelled with an energy donor and a second group labelled with an energy acceptor, where the donor is a luminescent lanthanide label capable of up-converting a lower-energy excitation to a higher-energy emission, where the acceptor is either a luminescent or a non-luminescent label, and where the increase or decrease, respectively, in energy transfer from the donor to the acceptor resulting from shortening or lengthening of the distance between the labels is measured. The assay is performed in a biological fluid which absorbs radiation in the wavelength range 300 to 600 nm, the measurement is carried out at a wavelength >570 nm, and the donor label, which is excitable at wavelength longer than its emission wavelength, is excited in the wavelength window in which the biological fluid does not essentially absorb the excitation radiation.

16 Claims, 8 Drawing Sheets

HOMOGENEOUS LUMINESCENCE ENERGY TRANSFER BIOASSAY

This application is a continuation-in-part of International Application PCT/FI2004/000091, filed Feb. 24, 2004, which claims priority of Finnish Patent Application 20030460, filed Mar. 28, 2003, and U.S. Provisional Application 60/540,300, filed Jan. 30, 2004.

FIELD OF THE INVENTION

This invention relates to measurement of analyte concentration or biological activity in biological fluid, only weakly transparent or non-transparent at visible wavelengths, using a luminescence energy transfer based homogeneous bioassay comprising a first group labelled with an energy donor and a second group labelled with an energy acceptor, wherein the donor is a luminescent lanthanide label being able to up-convert a lower-energy excitation to a higher-energy emission.

BACKGROUND OF THE INVENTION

The publications and other materials used herein to illuminate the background of the invention, and in particular, cases to provide additional details respecting the practice, are incorporated by reference.

Homogeneous Bioassay Technologies

Development of ever more simple, rapid, reliable and sensitive, quantitative bioassays has been one of the main objects in evolution of immunoassay, other ligand binding assay and biological activity assay techniques. Homogeneous immunoassay methods have received much attention, because they could speed up an assay by eliminating the need for cumbersome steps of separation of bound and free label, and significantly simplify construction of an instrument required to perform an assay automatically (Ullman E F, J Chem Ed 1999; 76:781-788; Ullman, E F, J Clin Ligand Assay 1999; 22:221-227). One of the major obstacles in the development of advanced, low-cost point-of-care instruments for immunoanalysis are the limitations of label technologies. Currently available label technologies suitable for homogeneous, non-separation immunoassays either suffer from interference of complex biological sample matrices, the technologies cannot be universally employed to different analytes and assay formats, e.g. both competitive and non-competitive assays, they simply do not enable sensitive assays enough to be performed using a rapid read-out, or the instrumentation required for detection is too complex or expensive to be employed in a point-of-care instrument.

Homogeneous assay methods based on photoluminescence have received much attention, since several types of physical and chemical interactions can be employed to modulate the emission of photoluminescent labels due to formation of specific immunological complexes. The commonly employed methods are based on polarization of the emitted light or nonradiative energy-transfer between two photoluminescent compounds or between a photoluminescent and a non-luminescent compound (Hemmilä I, Clin Chem 1985; 31:359-370). Fluorescence properties of two fluorescent compounds were employed in a homogeneous immunoassay in late 1970's when Ullman et al. demonstrated, that fluorescence energy transfer between fluorescein donor and tetramethylrhodamine acceptor pair could be employed to construct both competitive and non-competitive immunoassays (Ullman E F et al. J Biol Chem 1976; 251:4172-4178; Ullman E F & Khanna P L, Methods Enzymol 1981; 74:28-60). The energy transfer was measured from decrease in the fluorescence of donor, which limited further improvements in sensitivity. Increase in the fluorescence of the acceptor was not practicable, since only a little increase in a sensitised acceptor emission could be observed over autofluorescence, light scattering or absorbance of biological sample matrices and the direct emission of the donor at acceptor-specific wavelength.

Many compounds and proteins present in biological fluids or serum are naturally fluorescent, and the use of conventional fluorophores leads to serious limitations of sensitivity (Wu P and Brand L, Anal Biochem 1994; 218:1-13). Another major problem when using homogeneous fluorescence techniques based on intensity measurements is the inner filter effect and the variability of the optical properties of a sample. Sample dilution has been used to correct this drawback, but always at the expense of analytical sensitivity. Feasibility of fluorescence energy transfer in immunoassays was significantly improved when fluorescent lanthanide cryptates and chelates with long-lifetime emission and large Stokes' shift were employed as donors in the 1990's (Mathis G, Clin Chem 1993; 39:1953-1959; Selvin P R et al., Proc Natl Acad Sci U S A 1994; 91:10024-10028; Stenroos K et al., Cytokine 1998; 10:495-499; WO 98/15830; U.S. Pat. No. 5,998,146; WO 87/07955). Feasibility of the label technology in dissociation reactions, e.g. cleavage assays, has also been described (Karvinen J et al., J Biomol Screen 2002; 7:223-231).

Time-resolved fluorescence detection of sensitized emission allowed elimination of the autofluorescence and dual signal ratio measurement (U.S. Pat. No. 5,527,684; Mathis, G, Clin Chem 1993; 39:1953-1959) corrected the variability of optical properties of the sample. Fluorescence of the compounds and proteins present in biological fluids has a short lifetime and the use of long-lifetime labels combined with time-resolved detection of the sensitised (prolonged lifetime) acceptor emission allowed minimization of the assay background and improved signal to background ratio. The variability of absorption of excitation light at 337 nm was corrected by measuring the emission of the donor at 620 nm and using the ratio of the energy transfer signal at 665 nm and the emission at 620 nm to generate a variable that is independent of the optical properties of the serum sample.

Separation free assay technologies based on confocal detection of photoluminescent labels bound on particulate carriers have been introduced as an alternative to real homogeneous assays (Saunders G C et al., Clin Chem 1985; 31:2020-2023; Frengen J et al., Clin Chem 1993; 39:2174-2181; Fulton R J et al., Clin Chem 1997; 43:1749-1756). In recent years, the technology has been developed, and some novel carrier-based immunoassays can be considered as homogeneous assays, since they are practically similar to perform (Hanninen P et al., Nat Biotechnol 2000; 18:548; U.S. Pat. No. 5,891,738; Schaertl S et al., J Biomol Screen 2000; 5:227-238), although the actual signal of the label is not modulated, but the unbound labelled component is spatially excluded from measurement. These assay are otherwise comparable to homogeneous assays, but measurement is relatively slow, since carrier particles have to be either actively scanned or passively diffuse to focal point, and signal associated to several carrier particles is required for reliable measurement (Waris M E et al., Anal Biochem 2002; 309:67-74). Luminescence oxygen channelling immunoassay, LOCI, a true homogeneous assay based on particulate label pair and photoactivated chemiluminescence with up-conversion has been demonstrated with extreme sensitivity (Ullman E F et al., Clin Chem 1996; 42:1518-1526; Ullman E F et al., Proc Natl Acad Sci USA 1994; 91:5426-5430), but the reservations in the particle-particle pair formation and susceptibility to sample interferences have prevented the adaptation of the technology for routine diagnostic applications. To avoid sterical hindrance in binding at least one of the labels, preferably both labels of a label-pair should be of small molecular size.

The homogeneous assays techniques based on fluorescence labels would enable very rapid and simple assays using a single incubation method without any wash steps. In most of the conventional homogeneous fluorescence immunoassay technologies, the assay performance has still severe limitations: the sensitivity of the assays is limited by interferences from matrix components and optical properties of matrices, e.g. urine, saliva, serum, plasma or whole blood, to fluorescence yield and level of background, and by the attainable degree of fluorescence modulation, e.g. quenching, enhancement, energy transfer or polarization (Hemmilä I, 1985). Optical properties of biological matrices at visible wavelengths and in the near-infrared region are described in Chance B, Photon Migration in Tissues, pp. 206; Kluwer Academic/Plenum Publishers, 1990, New York. Fluorescence polarization assays utilizing fluorescence utilizing near-infrared fluorophores (U.S. Pat. No. 6,060,598) are limited to competitive binding assays. Ideally, the modulation of fluorescence signal should not restrict the type of assay, non-competitive or competitive, or type and molecular size of an analyte, and the modulation should stay detectable and preferable unchanged when a significant portion of the assay solution consists of biological matrix. These stringent requirements for a general and sensitive homogeneous fluorescence immunoassay explain, why the majority of developed assays have been limited to academic research, restricted to particular type of analyte and matrix, and have weak sensitivity and narrow dynamic range (Mathis G, 1993).

Long Lifetime Luminescent Labels

Employment of long-lifetime fluorescent lanthanide cryptates in homogeneous energy transfer immunoassay provided an improved assay technology, which solved most of the problems associated with the earlier homogeneous immunoassay methods. Time-resolved amplified cryptate emission (TRACE) technology is a general label technique enabling highly sensitive non-competitive assays and it is also suitable for competitive assays. The technology is applicable to serum samples only with correction of sample absorbance using simultaneous measurement of both the donor and the acceptor emission and it is not applicable to whole-blood samples. Although this technology has enabled rapid and simple immunoassay from serum with good precision, it has not been a commercial success. The instrument employed nitrogen laser to enable an extremely powerful and sharp excitation pulse and immediate opening the measurement window after an excitation pulse and resulted in excellent performance but expensive design of instrument. Further, the advantages of the rapid assay were partly diminished, as the technology was not suitable for whole blood and required preparation of serum sample.

Development of homogeneous whole blood analysis using photoluminescent proximity-based techniques requires selection of labels with excitation and sensitised emission at near-infrared window. In principle, suitable short-lifetime near-infrared fluorescent donor and acceptor dyes exist, but the autofluorescence and scattering still restrict the limit of detection (Oswald B et al., Anal Biochem 2000; 280:272-277), although pulsed laser or high-frequency modulated excitation and sub-nanosecond time-resolution in fluorescence detection (Augustin C. 2001, Ruthenium-ligand complexes as bioanalytical luminescent probes for polarization and energy transfer systems. Ph.D. Thesis, University of Regensburg, Germany, 119 pp.), available at high cost, would somewhat improve the sensitivity. Inexpensive instrumentation would be available for millisecond time-resolution, but unfortunately no perfect near-infrared fluorescent donor dyes are available with millisecond fluorescence lifetime. Neither near-infrared fluorescent lanthanide(III) chelates (Werts M H V. 2000. Luminescent lanthanide complexes: Visible light sensitised red and near-infrared luminescence. Ph.D. Thesis, University of Amsterdam, The Netherlands. 131 pp.), ruthenium(II) complexes (Augustin C M et al., Anal Biochem 2002; 305:166-172), phosphorescent platinum(II) and palladium(II) porphyrins (Soini A E et al., J Porphyrins Phthalocyanines 2001; 5:735-741) nor energy-transfer dyes (Lakowicz J R et al. Anal Biochem 2001; 288:62-75) provide all the required features, since they are excited either outside the near-infrared window or the emission peaks are at wavelengths over 850 nm, where no feasible acceptor dyes are currently available.

Anti-Stokes or Up-Converting Phosphors

Luminescent materials which can be excited by long-wave radiation, for example, infra-red radiation and then emit radiation having shorter wavelengths, particularly visible radiation are also called anti-stokes phosphors or up-converting phosphors. They are excited by sequential absorption of two or more photons of the exciting radiation. The excitation is thus effected in two or more stages so that the luminescent centres of the phosphors reach such a high energy level that photons emitted from the same are richer in energy than the exciting photons, i.e. the emitted radiation has a shorter wavelength than the exciting radiation. The two or more absorbed photons may have the same or different energy or wavelength and they may be produced by a single or multiple light sources.

The up-conversion differs from two-photon or multi-photon excitation based on simultaneous multi-photon absorption (U.S. Pat. No. 5,777,732, U.S. Pat. No. 5,523,573) as the absorption of multiple photons in the described method does not need to be simultaneous and significantly lower intensities of excitation light can be applied. Excitation of up-converting labels can be performed with e.g. pulsed halogen lamps or semiconductor light-emitting diodes or lasers, which are compact, have high power and are also inexpensive (Johnson B D, Photonics Spectra 2001; 35:52). The exciting radiation employed in the up-conversion is not sufficiently energetic to excite background emission from the sample or surroundings with multi-photon excitation at a wavelength, which would interfere with the measurement.

The up-converting phosphors has been known since 1970's, but their unique property of anti-stokes fluorescence has not been employed in biomedical research until 1990's (Corstjens P et al., Clin Chem 2001; 47:1885-1893; Niedbala R S et al., Anal Biochem 2001; 293:22-30; van De Rijke F et al., Nat Biotechnol 2001; 19:273-276; Zijlmans HJMAA et al., Anal Biochem 1999; 267:30-36).

Employment of long-lifetime particulate donor with short lifetime fluorescent acceptor in ligand binding assays is described in WO 02/44725, which also covers the use of anti-stokes phosphors as donors, but it does not relate to whole-blood analysis. The description of particulate-based homogeneous time-resolved assay in this patent application is partly overlapping with earlier patent applications, WO 00/23785 and WO 99/12018, which, however, do not consider the use of anti-stokes phosphors. The use of up-converting phosphors in separation based diagnostic applications has been described in WO 94/07142, U.S. Pat. No. 5,674,698, U.S. Pat. No. 6,159,686 and U.S. Pat. No. 6,312,914. The homogeneous assay principle based on up-converting phosphors has been described in WO 98/43072 and in more detail in US 2002/0119485. Up-converting chelates have been described in U.S. Pat. No. 5,891,656 and Faris G W and Hryndza M, Proc SPIE—Int Soc Opt Eng 2002; 4626:449-452. Method of separation of different lifetimes using cyclical excitation has been described in WO 99/63327.

Thus, these up-converting phosphors and up-converting chelates have been suggested for use in various assays, also homogeneous energy transfer assays, but so far they have not been suggested for use in homogeneous energy transfer assays to be carried out in whole blood, serum or plasma or other biological fluids, which absorb radiation in the wavelength range 300 to 600 nm and are difficult to be measured with current homogeneous bioassay technologies.

OBJECT AND SUMMARY OF THE INVENTION

The object of the present invention is to provide a luminescence energy transfer based homogeneous bioassay technology, suitable for use in bioassays to be carried out in biological fluids absorbing radiation in the wavelength range 300 to 600 nm, especially whole blood, serum or plasma. The aim is to achieve assays which are rapid and do not need any separation steps, which can be carried out in one step without interference from labels or components in the biological fluid, which can be carried out by inexpensive instrumentation, without need of temporal resolution between excitation and emission registration and without need of correction of variation in absorbance of sample matrices at excitation or emission wavelength.

The inventors of the present invention have discovered that the aforementioned objects can be achieved by the use of an up-converting luminescent lanthanide phosphor or up-converting rare earth chelate as donor label.

Thus, this invention concerns a luminescence energy transfer based homogeneous bioassay comprising a first group labelled with an energy donor and a second group labelled with an energy acceptor, wherein
   the donor is a luminescent lanthanide label, said label being able to up-convert a lower-energy excitation to a higher-energy emission,
   the acceptor is either a luminescent or a non-luminescent label, and
   the increase or decrease, respectively, in energy transfer from the donor to the acceptor resulting from shortening or lengthening, respectively, of the distance between said labels is measured.

According to the invention,
   the assay is performed in a biological fluid which absorbs radiation in the wavelength range 300 to 600 nm,
   the measurement is carried out at a wavelength >570 nm, and
   the donor label, which is excitable at wavelength longer than its emission wavelength, is excited in the wavelength window in which the biological fluid does not essentially absorb the excitation radiation.

The quenched luminescence of the donor, or the sensitized emission of the luminescent acceptor, are measured in the wavelength window in which the biological fluid does not essentially absorb the emission radiation, and thus does not disturb the measurement.

The invention provides a unique combination of features for homogeneous, non-separation bioassays based on luminescent detection:

1) signal of the assay (sensitised accepter emission or quenched donor emission) is strictly dependent on the distance between two labels, donor and acceptor, as the efficiency of the fluorescence resonance energy transfer is dependent to inverse sixth power of distance.

2) signal of the assay is independent of the biological sample matrix, since both the excitation and the emission wavelengths are at the near-infrared region.

3) signal of the assay can be measured with spectral resolution only, i.e. without need for temporal resolution, since biological material does not produce anti-stokes luminescent background.

4) the label technology is suitable for both competitive and non-competitive ligand binding assays, both for large and small analyte molecules, because one or both of the label moieties can be of small molecular size.

These features enable sensitive universal bioassays to be performed using minimally diluted whole-blood samples (and other biological fluids) and simple, inexpensive instrumentation without temporal resolution or correction of variation in optical properties of sample, providing an ideal platform for e.g. point-of-care immunoassay methods.

The up-converting lanthanide phosphors convert infrared to visible light via sequential absorption of two low-energy photons, which is a truly unique feature and does not exist anywhere else in nature, and evidently no background fluorescence or scattering is produced by any biological fluids at the phosphor specific visible wavelength with infrared excitation. The up-converting label provides enhanced signal-to-noise ratio and total elimination of background sample autofluorescence. The optical properties of the up-converting phosphors are completely unaffected by the environment, since the up-conversion process occurs solely within the up-converting phosphor crystal.

The excitation of these up-converting phosphors, unlike two-photon excitation, does not require extremely high laser power, since the two or more photons do not need to be absorbed simultaneously.

These anti-stokes luminescent compounds, up-converting lanthanide phosphors or up-converting lanthanide chelates, could be employed as donors in homogeneous bioassays, including immunoassays, similar to long-lifetime rare earth chelates in time-resolved fluorescence resonance energy transfer assay, but without need for temporal resolution or ultraviolet excitation and correction of variation in optical properties of the sample, providing all of the features for an ideal label technology. Actually, the anti-stokes measurement should enable improved elimination of background with simple band-pass optical filters compared to time-resolved detection requiring in addition temporal resolution.

DETAILED DESCRIPTION OF THE INVENTION

Definitions

The terms "first group" and "second group", which both are labelled, shall be understood to include any component such as bioaffinity recognition component (in reactions where the distance between the groups decreases, e.g. in bioaffinity reactions) or a part of a molecule or substrate (e.g. distal ends of a peptide molecule the cleavage of which will separate the two labelled groups from each other).

The term "bioassay" shall be understood to include association assays, i.e. bioaffinity assays, such as immunoassays and nucleic acid hybridization assays in which the distance between the labelled groups decreases. Furthermore, this term covers dissociation assays, such as cleavage assays in which the distance between the labelled groups increases.

The term "immunoassay" shall be understood to include competitive and non-competitive ligand binding assays based on polyclonal or monoclonal antibodies, receptors, recombinant antibodies or antibody fragments as well as artificial binders like aptamers and engineered proteins.

The term "homogeneous bioassays" shall be understood to cover bioassays requiring no separation steps. Single or multiple steps of each; addition of reagents, incubation and measurement, are the only steps required.

The term "luminescence" shall be understood to cover photoluminescence, i.e. fluorescence, including delayed fluorescence with microsecond or millisecond fluorescence lifetime, and phosphorescence. Long-lifetime luminescent compounds shall be understood to have a luminescence lifetime over 1 microsecond (time when luminescence emission intensity decays to relative value 1/e, i.e. approximately 37% of the luminescence emission intensity is left) and compounds with luminescence lifetime below that are referred as short-lifetime luminescent compounds.

The terms "luminescent lanthanide label" and "lanthanide label" shall be understood to include a lanthanide chelate or chelate structure, containing one or more lanthanide ions, an inorganic lanthanide containing phosphor particle, or a polymeric nanoparticle containing either the described lanthanide chelates or phosphor particles. The lanthanide can represent one single lanthanide element or a combination of several different lanthanide elements.

The term "lanthanide" shall be understood here equivalent to "rare earth metal ion" and to include single lanthanide elements and combination of several different lanthanide elements from the following: neodymium, praseodymium, samarium, europium, promethium, gadolinium, terbium, dysprosium, holmium, erbium, thulium, ytterbium and yttrium, especially erbium, praseodymium, thulium, and ytterbium.

The term "up-conversion" means photoluminescent process converting lower energy incident light to higher energy emitted light. It is also called anti-stokes photoluminescence. Anti-stokes photoluminescence material converts low energy light to high energy light. In "up-conversion" two or more lower energy photons of the same or different energy are absorbed sequentially, in two or more stages, to generate a single higher energy photon, in contrary to simultaneous absorption in two-photon or multi-photon excitation.

The term "up-converting lanthanide label" shall be understood to as photoluminescent lanthanide compound with up-conversion, i.e. luminescent lanthanide label being able to up-convert a lower energy excitation to a higher-energy emission based on an excitation in two or more stages: it means that two or more photons are sequentially absorbed to excite the label, in contrary to simultaneous absorption in two or three photon excitation. The up-converting lanthanide labels include up-converting lanthanide phosphors and up-converting lanthanide chelates.

The term "up-converting lanthanide chelate" means here up-converting lanthanide label, where a single rare earth ion or combination of different rare earth ions is chelated to mono or multinuclear complexing ligand or multiple ligands. The ligand may or may not contain light harvesting structure. The light collection efficiency of individual ions and chelated ligands without light harvesting structure is poor. Therefore, up-converting rare earth chelates can be designed to contain ligand with light-harvesting organic or inorganic structures, e.g. another ion, incorporated. The collected energies of two or more photons are transferred one after another by intramolecular non-radiative processes from the singlet to the triplet state of the organic structure, then from the triplet state sequentially to the emissive level of the rare earth ion, which then emits a single photon of characteristic emission.

The term "up-converting lanthanide phosphor" shall be understood as particulate luminescent lanthanide label capable to up-conversion, wherein the particulate absorbs long wavelength radiation and emit light at shorter wavelength as result of energy pooling of sequential absorption of long wavelength radiation. In certain types of phosphors, a priming dose of energy at shorter wavelength is required to excite and pre-load the phosphor before the up-conversion of long wavelength radiation is possible. The up-converting phosphor can be able to delocalise its excitation from a part or the entire volume of the particulate by internal transfer of energy between similar excited states within the particulate to a single or a few acceptor molecules. This means that a single acceptor can be excited by lanthanides which would otherwise be too far away for energy transfer to be efficient.

The terms "donor" and "donor label" shall be understood as up-converting luminescent compound (attached to the first or the second group of bioassay) capable of energy transfer to acceptor when in sufficiently close proximity.

The terms "acceptor" and "acceptor label" means luminescent or non-luminescent compound (attached to the first or the second group of bioassay) having absorption spectra at least partially overlapping with the emission spectra of the donor and capable of energy transfer from the donor.

The term "biological fluid" means any biological fluid which absorbs radiation in the wavelength range 300 to 600 nm, but particularly whole blood, serum, plasma, saliva, urine, suspended feces, seminal plasma, sweat, liquor, amniotic fluid, tissue homogenate or ascites. The biological fluid refers especially to whole blood, serum or plasma, particularly whole blood.

The biological fluid can be the fluid as such or diluted. Thus, for example, the term "whole blood" shall be understood to include also "diluted whole blood".

Figure 1:
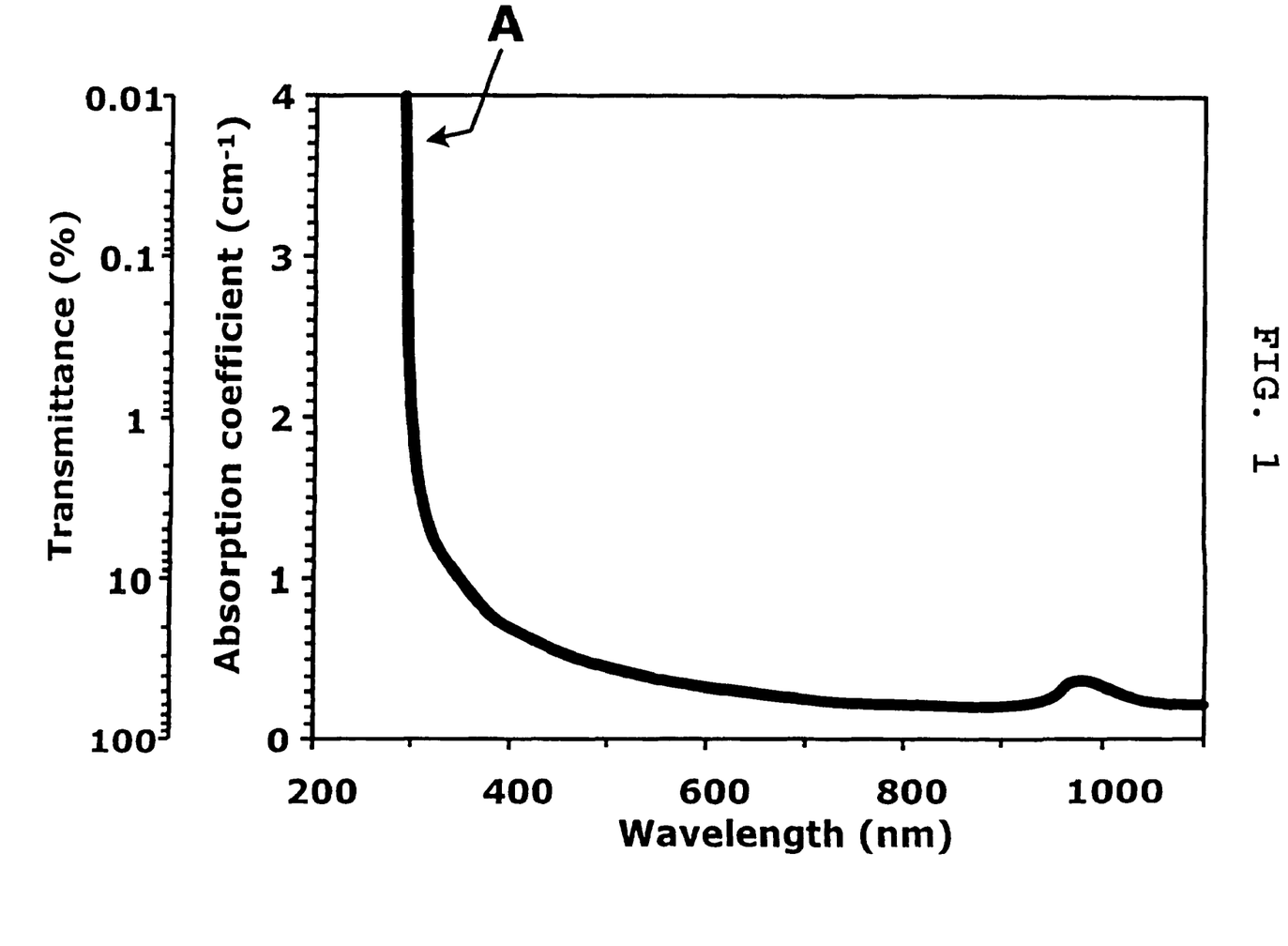
FIG. 1 shows the absorption spectrum of human serum (A; 1:10 dilution in saline). Human serum is relatively transparent at 400-1100 nm.
Figure 2:
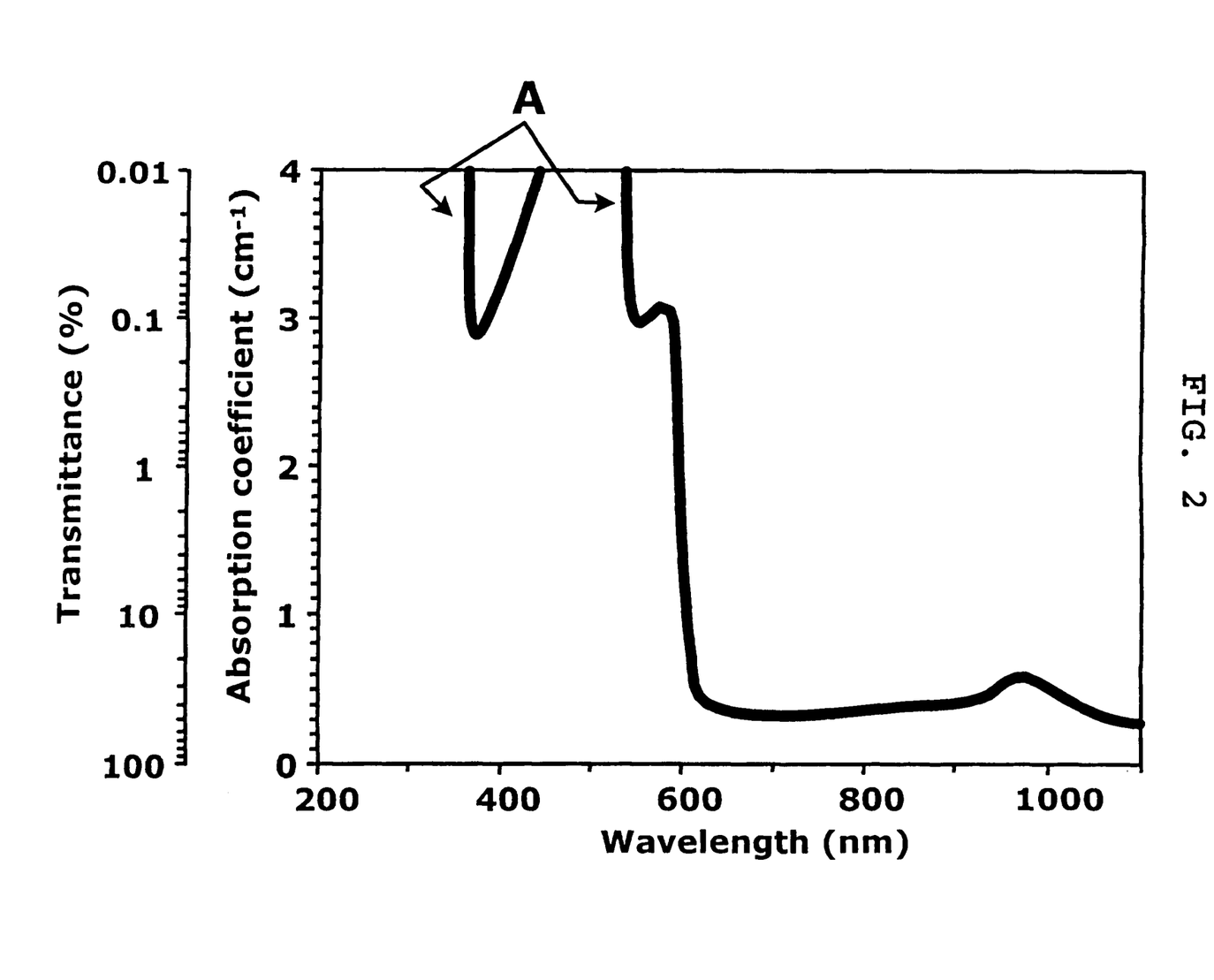
FIG. 2 shows the absorption spectrum of human whole blood (A; 1:10 dilution in saline). Human whole blood is relatively transparent at 600-1100 nm.
Figure 3:
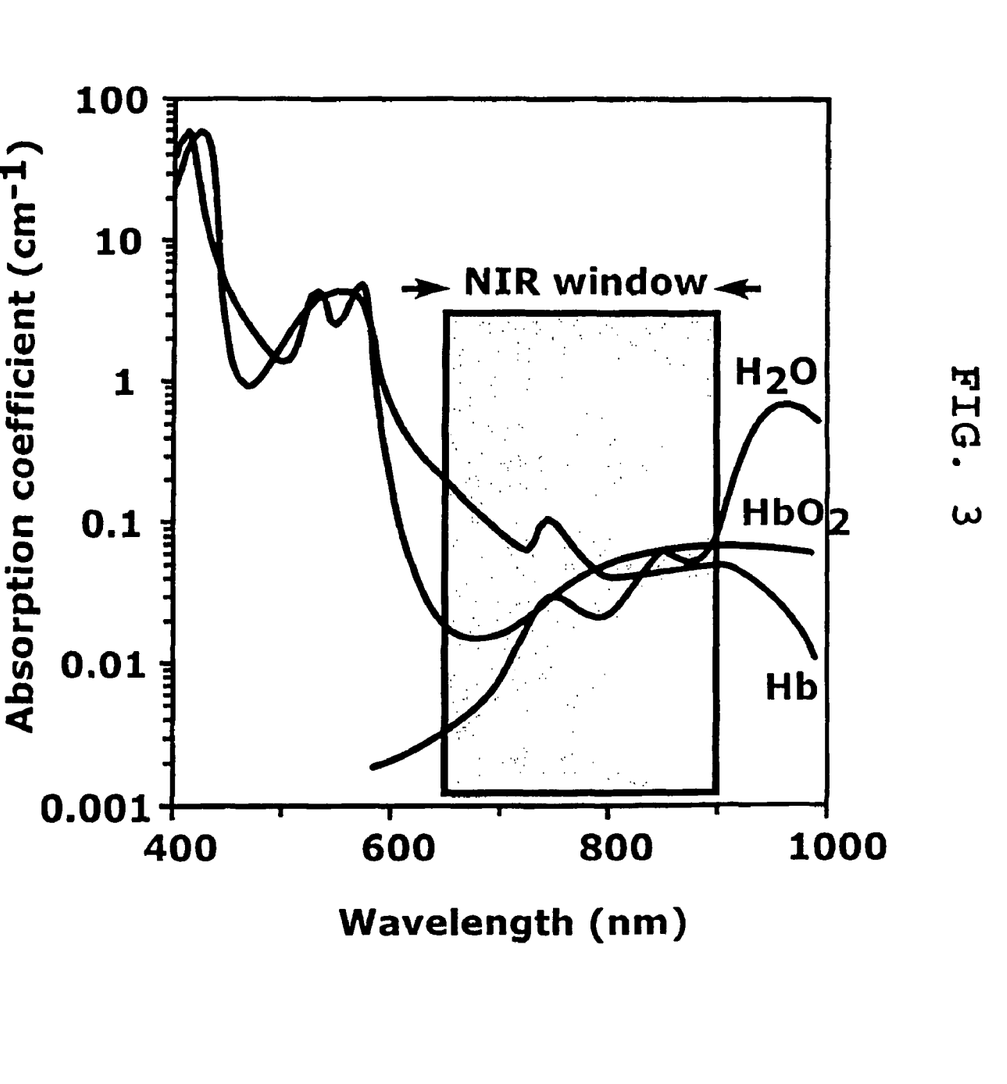
FIG. 3 shows the near-infrared (NIR) window (the wavelength range from 650 to 900 nm). The figure shows that hemoglobin (Hb) and water ($H_2O$) have their lowest absorption coefficients within the NIR window.

Biological fluids such as serum, plasma and even whole blood are relatively transparent to light in the wavelength range 600 to 1000 . . . 1100 nm (human serum even at lower wavelengths, see FIG. 1), especially in the near-infrared window between 650-900 nm. Proteins and nucleic acids are strongly absorbing in the ultraviolet region and absorption of many proteins, especially hemoglobin, continues up to wavelengths around 650 nm (see FIG. 2, which shows the absorption spectrum of human whole blood, and FIG. 3 which shows the absorption of oxy- and deoxyhemoglobin and water as function of wavelength, where the most transparent wavelength range for whole blood, the near-infrared (NIR) window also is indicated). Water absorbs photons weakly at wavelengths longer than 900 nm and absorption of water becomes dominant at wavelengths longer than 1150 nm. In practice, only wavelengths in the window 600 to 1100 nm, or more preferably in the near infrared window 650 to 900 nm, are practicable when a whole blood sample is employed.

The measurement is preferably carried out at a wavelength >600 nm.

Preferred Donor Labels

The up-converting or anti-stokes luminescent lanthanide for use as donor label shall thus be excitable at a wavelength below the wavelength where the absorption by water becomes dominant, i.e. below 1150 nm, preferably below 1100 nm, and most preferably below 900 nm.

In case the acceptor label is a non-luminescent label which quenches the emission of the donor label when the labels are in close proximity, then it is also necessary that the emission of the up-converting luminescent lanthanide label takes place at a wavelength above the limit where the absorption by proteins and nucleic acids becomes dominant, i.e. preferably above 600 nm, especially above 650 nm.

In case the acceptor label is a luminescent label, then the emission of the up-converting luminescent lanthanide label could take place at a wavelength below the limit where the absorption by components of biological fluid becomes dominant, because the acceptor label will emit at a higher wavelength than the emission wavelength of the donor.

The most promising anti-stokes lanthanide phosphors have narrow emission bands at green (550 nm) and red (670 nm), similar to other long-lifetime luminescent lanthanide ions like europium and terbium, and they are excited at the upper limit of the near-infrared window at 950-1000 nm. The narrow emission bands are preferred for energy-transfer assays, which require low direct emission of the donor at the acceptor specific wavelength. Optical properties of the phosphors are unaffected by their environment, e.g. buffer pH or assay temperature, since the up-conversion process occurs with the host crystal.

Figure 4A:
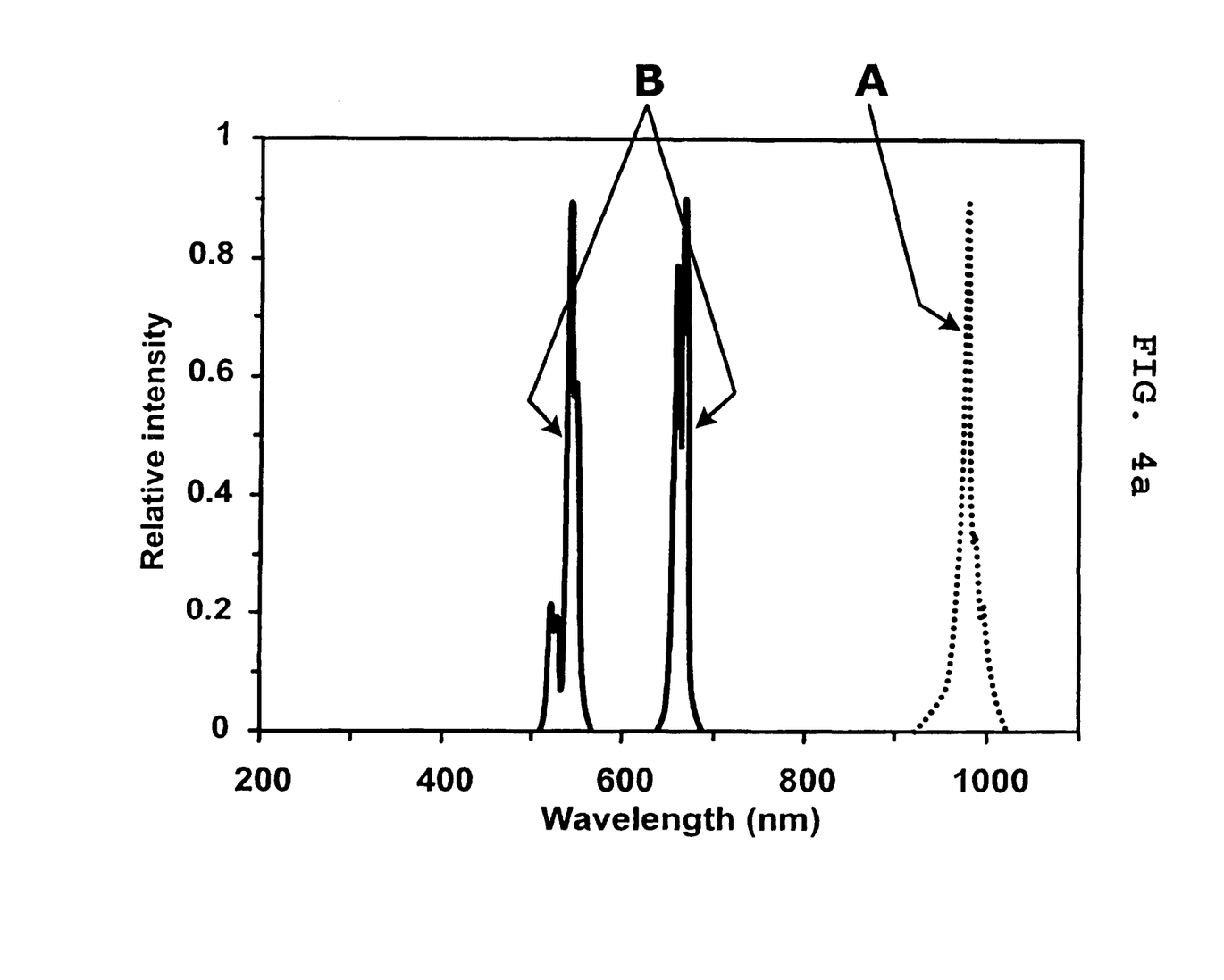
FIG. 4a shows the excitation (A; dotted line) and emission (B; solid line) spectra of a preferred up-converting phosphor (Er(III) doped Yb(III) phosphor) and 4b shows FIGS. 4a and 5 (Alexa 660; (2)) inserted in FIG. 2.
Figure 4B:
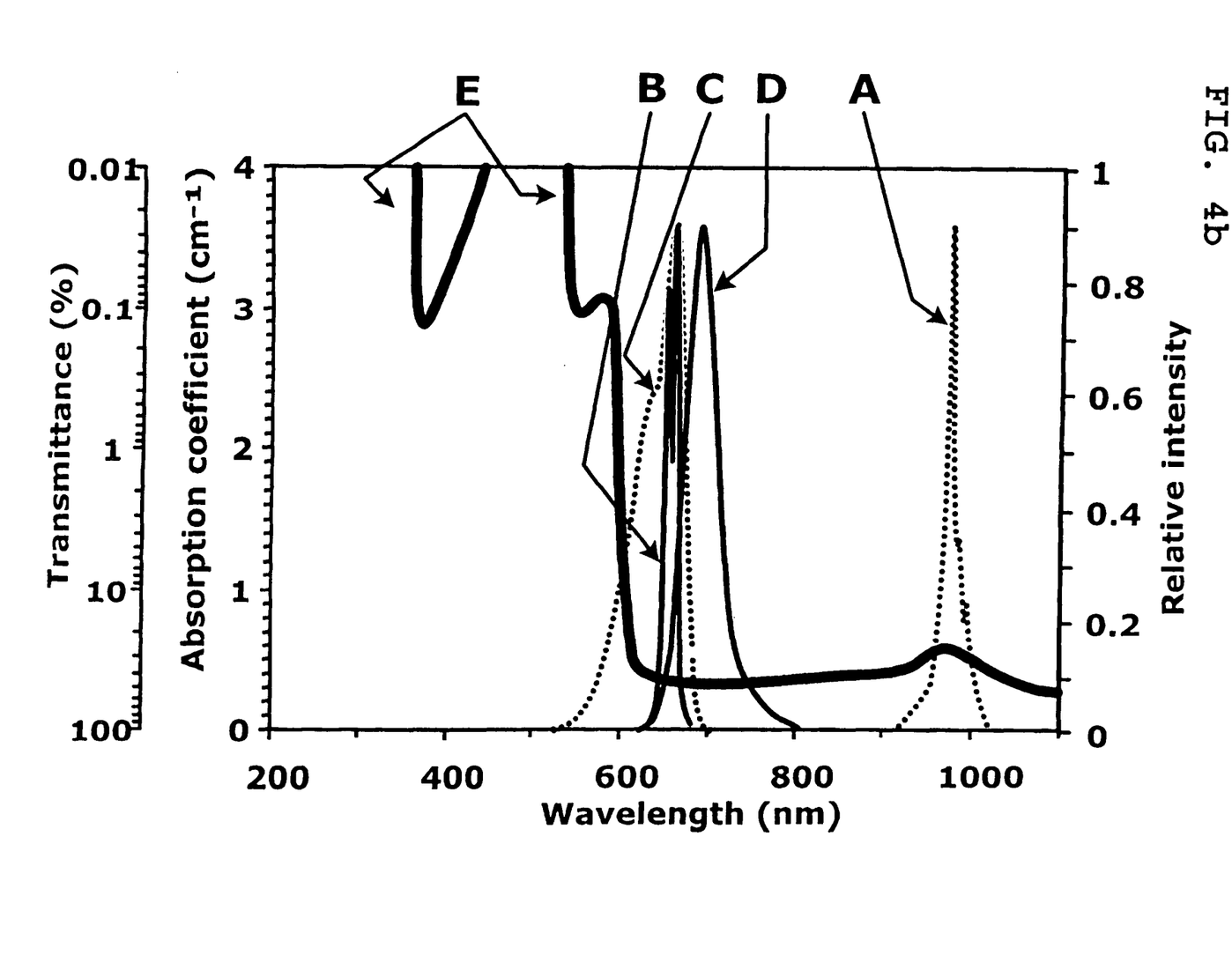
In FIG. 4b major excitation (A) and emission (B) bands of donor are shown in combination with excitation (C) and emission (D) spectra of the acceptor Alexa 660 and absorption spectra of the whole-blood (E; 1:10 dilution in saline).

A particularly preferred anti-stokes phosphor is shown in FIG. 4a, which shows the excitation (A; dotted line) and emission (B; solid line) spectra of up-converting Er(III) doped Yb(III) phosphor. Phosphor is in a form of fine particles. Excitation is most effective at 930-1010 nm. Narrow emission bands are observed at 510-560 nm and at 640-680 nm. FIG. 4b shows that (A) the excitation as well as (B) the narrow emission band at 640-680 nm of this donor label takes place in the transparent wavelength range of human whole blood; (E) the absorption spectra of anti-coagulated whole blood sample diluted in saline. The described donor label is suitable to be used in combination with the acceptor label Alexa 660 with (C) excitation band at 663 nm and (D) wide emission band extending to wavelengths above 690 nm.

As examples of other suitable up-converting lanthanide donor labels for use in this invention can be mentioned combinations of ytterbium with other lanthanides such as praseodymium, thulium, holmium or terbium. Several suitable phosphors are provided by e.g. LUMINOPHOR Joint Stock Company, LUMITEK International and Phosphor Technology Ltd.

According to a preferred embodiment, the donor label is a particle or embedded in a particle. The diameter of the particle is preferably in the range 1 nm to 1 µm.

According to another preferred embodiment, the donor label is a up-converting lanthanide chelate.

Preferred Acceptor Labels

In case the acceptor label is a luminescent label, it is excited by absorption of light at shorter wavelength than the light is emitted, and the difference is known as Stokes' shift. Luminescent acceptor label is preferably excited by absorption of light at the wavelength of major or significant emission of a donor label, and it preferably emits at a wavelength of none or minimal emission intensity of a donor label. Criteria for selection are described in WO98/15830 and U.S. Pat. No. 5,998,146. The overlapping of the donor emission spectra and the excitation spectra of the acceptor is not an unconditional requirement.

In case the acceptor label is a non-luminescent label, it preferably absorbs light at the wavelength of major or significant emission of a donor label.

Energy from a donor label can be transferred to one or more acceptor labels or to one or more particles containing one or more acceptor labels of the same or different types of acceptor labels.

Luminescent acceptor label can be a single luminescent molecule or combination of different luminescent molecules selected to allow an increased Stokes' shift. The preferred luminescent acceptor label is selected from the group consisting of rapidly decaying, short-lifetime fluorophores (fluorescence lifetime below 1 microsecond), semiconducting materials (Chan W C and Nie S, Science 1998; 281:2016-2018) such as quantum dots available from Quantum Dot Corp and polymeric particles embedded with any or any of combination of these (U.S. Pat. No. 5,326,692; Roberts D V et al. J Lumin 1998; 79: 225-231; Han M et al., Nat Biotechnol 2001; 19:631-635) available from Molecules Probes under the trademarks FluoroSpheres® and TransFluoroSpheres®. The luminescent acceptor label or a part of it can also be a near-infrared fluorescent protein (Trinquet E et al. Anal Biochem 2001; 296:232-244; Kronick M N, J Immunol Methods 1986; 92:1-13; Fradkov A F et al., FEBS Lett 2000; 479:127-130).

The preferred size of the acceptor particle ranges from 1 nm to 1 µm in diameter.

Especially suitable acceptor fluorophores are e.g. Alexa and BODIPY series available from Molecular Probes, Cy-dyes from Amersham Biosciences, EVOblue and DY-dyes from Dyomics, Atto-Dyes from Atto-tec and Oyster-dyes from Denovo Biolabels. Dimeric fluorescent energy transfer dyes, tandem dyes and energy-transfer cassettes, comprising two fluorescent molecules are preferred for their property of large and tunable Stokes' shift (U.S. Pat. No. 5,565,554; WO9939203; EP 0747700 A2; Burghart, A et al., Chem Commun 2000; 22: 2203-2204) enable utilization of optimal excitation and emission wavelengths.

Figure 5:
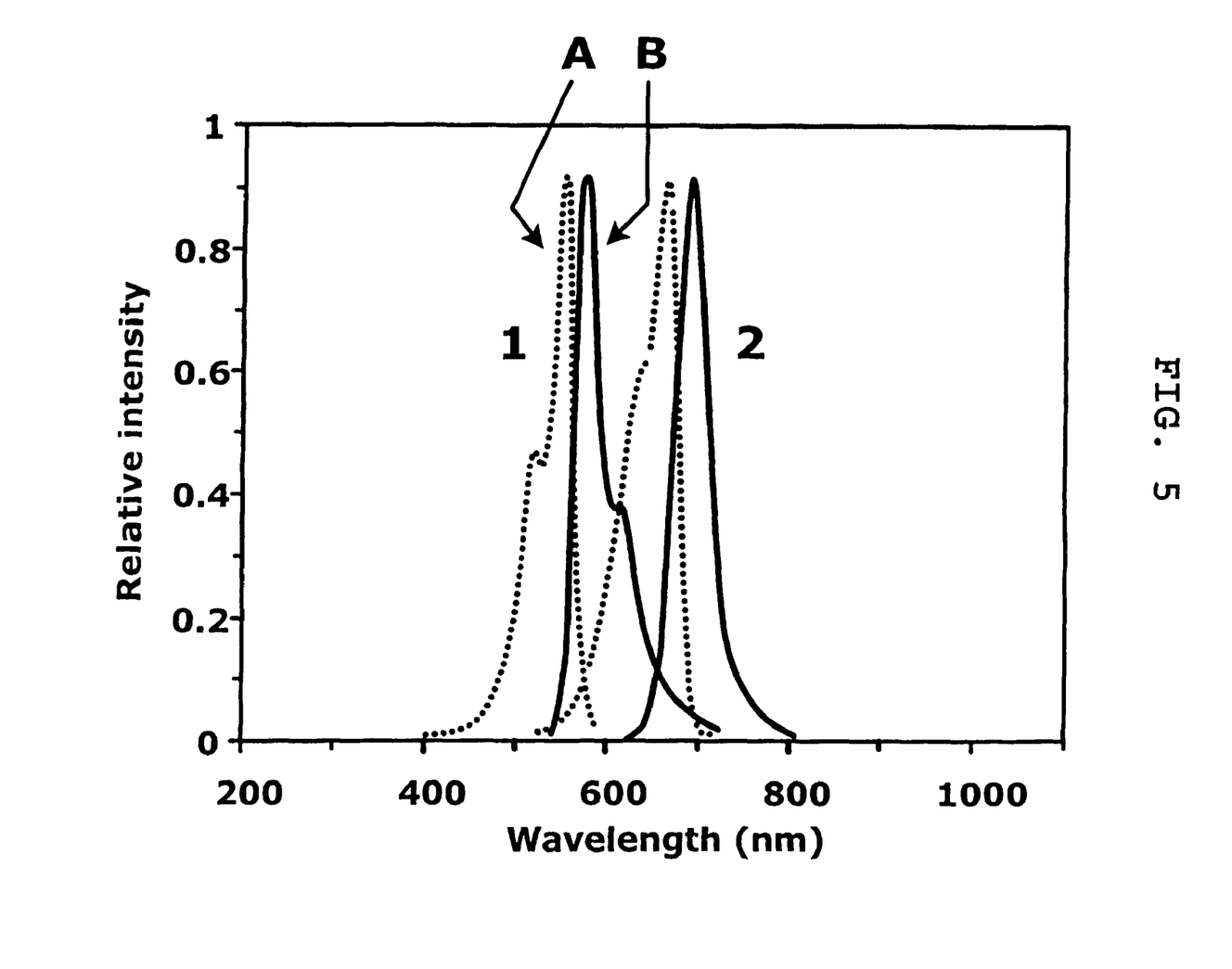
FIG. 5 shows the excitation (A; dotted lines) and emission (B; solid lines) spectra of two short lifetime fluorescent acceptor dyes, Alexa 555 (1) and Alexa 660 (2).

As specific examples can be mentioned Alexa 546, Alexa 555, Alexa 660 and Alexa 680, which are suitable to be used as acceptor label together with described up-converting erbium labels as donor label. The preferable acceptor label should be selected to have an excitation spectrum with overlaps at least partially with peaks of the emission spectrum of the donor label and has an emission maximum between the emission and acceptor wavelengths of the donor. FIG. 5 shows the excitation (A; dotted lines) and emission (B; solid line) spectra of two preferred fluorescent dyes, Alexa 555 (1) and Alexa 660 (2). Alexa 555 (molecular weight approximately 1250) has wide excitation and emission bands with maxima at 555 and 565 nm, respectively, and yet significant emission above 600 nm, and Alexa 660 (molecular weight approximately 1100) at 663 nm and 690 nm, respectively, with yet significant emission above 700 nm.

The up-converting label and the luminescent acceptor label can be selected so that both the excitation and the emission of the up-converting label and the optional sensitised emission of the acceptor label are at wavelengths with minimal absorbance and interferences of variation in optical properties of biological samples. Up-converting labels in combination with an acceptor label enable homogeneous assays to be performed regardless of the sample matrix enabling almost identical signal levels requiring none correction of the absorption when buffer based standards and biological fluids are employed.

Non-luminescent acceptor label, i.e. quencher label, can be a single molecule (U.S. Pat. No. 6,329,205B1), gold cluster (Dubertret B, Calame N, and Libchaber A J, Nat Biotechnol. 2001; 19:365-70) or nanoparticle dyed with light absorbing molecules. Especially suitable acceptor fluorophores are e.g DABCYL and QSY-series from Molecular Probes, Dark Cy-dyes from Amersham Biosciences, Eclipse™ Dark Quencher-dyes from Epoch Biosciences, Black Hole Quencher®-dyes from Biosearch Technologies, DYQ-dyes from Dyomics and ElleQuencher from Oswel. As specific examples can be mentioned QSY-21 and Black Hole Quencher 3, which are suitable to be used as non-luminescent acceptor label together with described up-converting erbium labels as donor label. Both dyes have strong absorption at 600-700 nm and have no luminescence emission.

OTHER PREFERRED EMBODIMENTS

Figure 6:
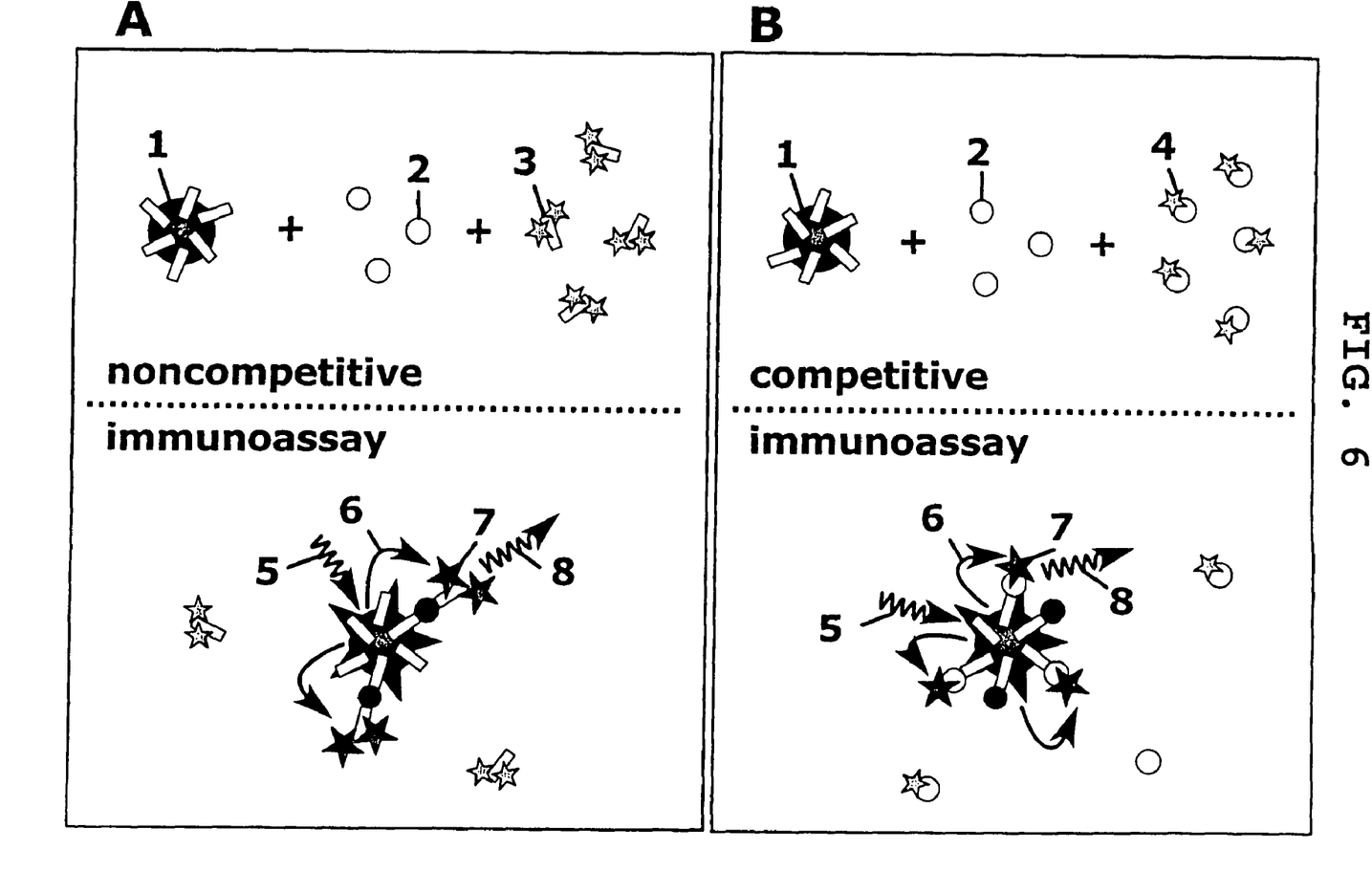
FIG. 6 shows the basic principles of (A) non-competitive and (B) competitive immunoassays based on up-converting luminescence proximity assay, when the donor is a particulate upconverting lanthanide label.
Figure 7:
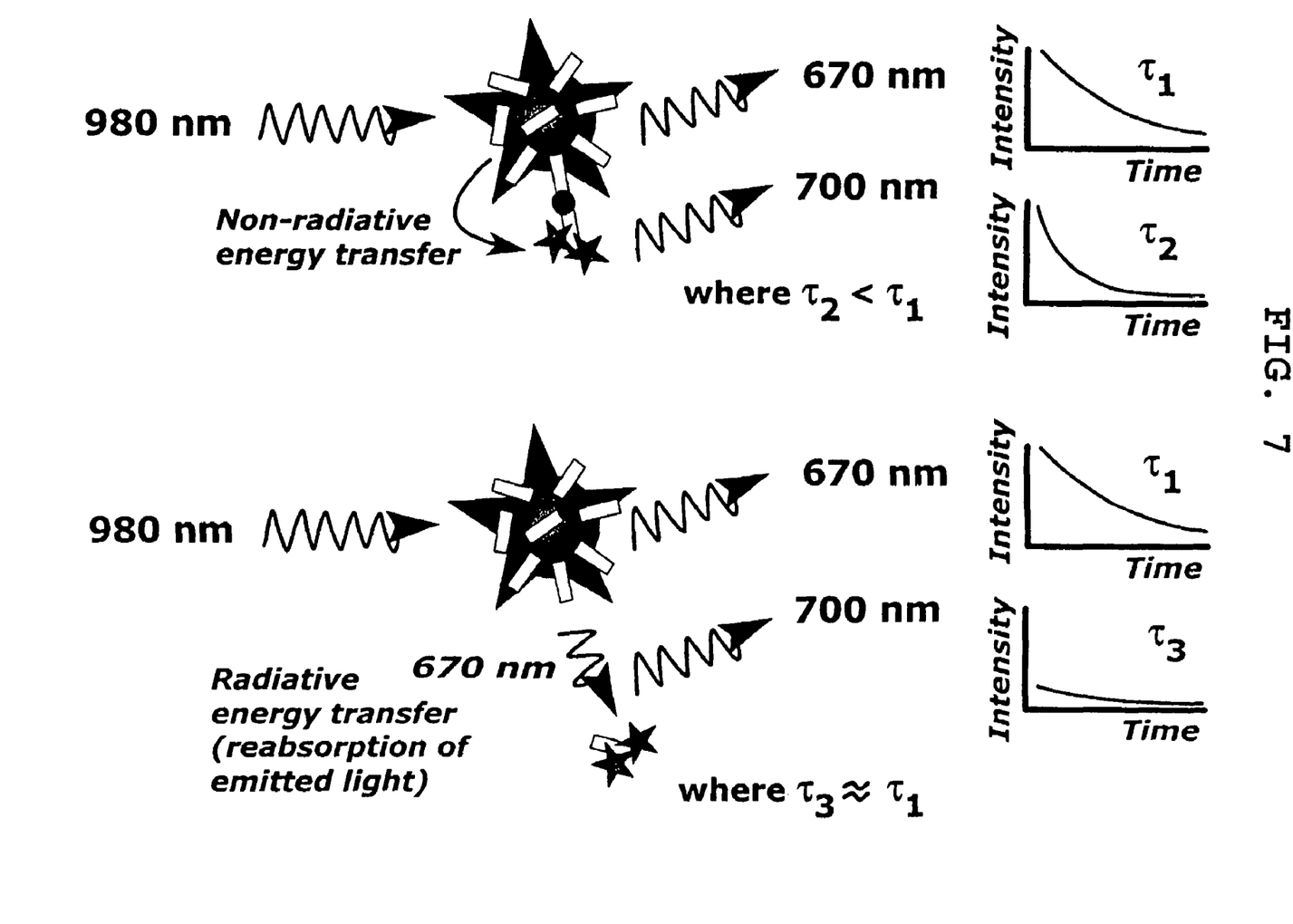
FIG. 7 shows an illustration of the differences in lifetimes of the sensitized acceptor emission (tau2; non-radiative energy transfer) and radiative background emission (tau3; reabsorption of emitted light).

The bioassay according to this invention can be either a non-competitive assay or a competitive assay. FIG. 6 shows the basic principles of (A) non-competitive and (B) competitive binding assays based on up-converting luminescence proximity assay: (1) a up-converting phosphor label, e.g. submicron size particulate or up-converting lanthanide chelate, (donor) coated with an analyte specific antibody fragment; (2) an analyte; (3) a near-infrared fluorescent (acceptor) labeled antibody fragment against analyte; (4) a near-infrared fluorescent (acceptor) derivative of analyte or analogue of analyte; (5) excitation of the up-converting lanthanide label (donor) at specific wavelength; (6) fluorescence resonance energy-transfer between donor and acceptor in proximity; (7) sensitized acceptor with prolonged fluorescence lifetime if the donor is long-lifetime luminescent compound; and (8) sensitized emission of the luminescent acceptor at acceptor specific wavelength. Although time resolution is not necessary in the method according to this invention, it is applicable, if desired. In particular, sensitivity of the rapid assays utilizing high concentration of the labeled components is restricted by the luminescence background at acceptor specific wavelength resulting from radiative energy transfer between donor and acceptor labels in solution, as illustrated in FIG. 7. The light emission resulting radiative and nonradiative energy transfer, respectively, differ in their lifetimes, tau3 and tau2, respectively, and the radiative energy transfer can be excluded with temporal resolution and separation of components of different lifetimes in luminescence emission. The luminescence lifetime of the light emission resulting from non-radiative energy transfer (tau2) is shorter (Heyduk T and Heyduk E, Anal Biochem 2001; 289:60-67; Selvin P R et al., J Am Chem Soc 1994; 116:6029-6030) than the lifetime of the light emission from the radiative energy transfer (tau3) and direct emission of the donor (tau1). The lifetimes can be separated using pulsed excitation and time-gated detection, or alternatively, using excitation modulated in intensity and analysis of the phase-shifted luminescence emission. The separation of lifetimes allows also discrimination against any short-lived background, which might be excited by two-photon or multiphoton excitation with high intensity light sources.

Although no correction of the absorbance is necessary in this invention, such correction could also be applied, if desired.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A luminescence energy transfer homogeneous bioassay comprising subjecting a first group labelled with an energy donor and a second group labelled with an energy acceptor to a reaction affecting the distance between said first group and said second group, wherein
   the donor is a luminescent lanthanide label which up-converts a lower-energy excitation to a higher-energy emission,
   the acceptor is either a luminescent or a non-luminescent label, and
   the increase or decrease, respectively, in energy transfer from the donor to the acceptor resulting from shortening or lengthening, respectively, of the distance between said labels is measured, wherein
   the assay is performed on a sample which comprises a biological fluid which absorbs radiation in the wavelength range 300 to 600 nm,
   the measurement of the acceptor emission or the donor emission is carried out at a wavelength >570 nm, and
   the donor label, which is excitable at wavelength longer than its emission wavelength, is excited at a wavelength longer than 600 nm.

2. The bioassay according to claim 1, wherein the measurement of the acceptor emission or the donor emission is carried out at a wavelength >600 nm.

3. The bioassay according to claim 1, wherein the acceptor label is a non-luminescent label, and the emission of the donor label has a wavelength greater than 600 nm.

4. The bioassay according to claim 1, wherein the acceptor label is a luminescent label, and the emission of the acceptor label has a wavelength greater than 600 nm.

5. The bioassay according to claim 1, wherein the biological fluid is selected from the group consisting of whole blood, serum, plasma, saliva, urine, suspended feces, seminal plasma, sweat, liquor, amniotic fluid, tissue homogenate and ascites.

6. The bioassay according to claim 5, wherein the biological fluid is selected from the group consisting of whole blood, serum and plasma.

7. The bioassay according to claim 5, wherein the biological fluid is whole blood and the donor excitation has a wavelength within the range 600 to 1100 nm.

8. The bioassay according to claim 7, wherein the biological fluid is whole blood and the donor excitation is in a wavelength within the range 650 to 900 nm.

9. The bioassay according to claim 7, wherein the acceptor label is a luminescent label which emits in the wavelength range 600 to 1100 nm.

10. The bioassay according to claim 9, wherein the acceptor label is a luminescent label which emits in the wavelength range 650 to 900 nm.

11. The bioassay according to claim 1, wherein the donor label is a luminescent lanthanide chelate.

12. The bioassay according to claim 1, wherein the donor label is a luminescent lanthanide phosphor particle or embedded in a particle.

13. The bioassay according to claim 1, wherein the bioassay is an immunoassay for the detection or quantification of an analyte, wherein the donor label is applied on a particle bearing an analyte-specific first antibody or antibody fragment, and the acceptor label is applied either i) on a second analyte-specific antibody or antibody fragment, wherein the immunoassay is carried out as a non-competitive assay, or ii) on an analyte-analogue, wherein the immunoassay is carried out as a competitive assay.

14. The bioassay according to claim 13, wherein the particle is in the range 1 nm to 1 μm in diameter.

15. The bioassay according to claim 1, wherein the donor has a long excited state lifetime, the acceptor has a short excited state lifetime, and the emission of the acceptor is measured after a delay.

16. The bioassay according to claim 1, wherein no correction of the absorbance is employed.

* * * * *

UNITED STATES PATENT AND TRADEMARK OFFICE
CERTIFICATE OF CORRECTION

PATENT NO. : 7,569,355 B2  
APPLICATION NO. : 11/148315  
DATED : August 4, 2009  
INVENTOR(S) : Soukka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this

Seventh Day of September, 2010

David J. Kappos  
*Director of the United States Patent and Trademark Office*